United States Patent
Nagamatsu et al.

[11] Patent Number: 6,117,343
[45] Date of Patent: Sep. 12, 2000

[54] FILLER-PACKING APPARATUS, FILLER-PACKING METHOD, AND FILLER-PACKED COLUMN ASSEMBLY

[75] Inventors: Shinji Nagamatsu, Niigata-ken; Koichi Murazumi, Hyogo-ken, both of Japan

[73] Assignee: Daicel Chemical Industries, Ltd., Osaka, Japan

[21] Appl. No.: 09/091,890

[22] PCT Filed: Dec. 19, 1996

[86] PCT No.: PCT/JP96/03708

§ 371 Date: Jun. 26, 1998

§ 102(e) Date: Jun. 26, 1998

[87] PCT Pub. No.: WO97/24612

PCT Pub. Date: Jul. 10, 1997

[30] Foreign Application Priority Data

Dec. 28, 1995 [JP] Japan ................................. 7-343732

[51] Int. Cl.[7] .................................................. B01D 24/38
[52] U.S. Cl. ...................... 210/807; 210/232; 210/282; 210/287; 210/341
[58] Field of Search ...................... 210/807, 232, 210/268, 270, 282, 287, 288, 340–345

[56] References Cited

U.S. PATENT DOCUMENTS

| | | | |
|---|---|---|---|
| 3,831,555 | 8/1974 | Srinivas | 118/506 |
| 4,093,550 | 6/1978 | Stahl et al. | 210/287 |
| 4,187,177 | 2/1980 | Stahl | 210/287 |
| 4,483,773 | 11/1984 | Yang | 210/656 |
| 5,102,553 | 4/1992 | Kearney et al. | 210/659 |
| 5,169,522 | 12/1992 | Shalon et al. | 210/241 |
| 5,624,553 | 4/1997 | Ladisch et al. | 210/232 |
| 5,846,829 | 12/1998 | Worden et al. | 210/807 |

FOREIGN PATENT DOCUMENTS

| | | |
|---|---|---|
| 0330503 | 8/1989 | European Pat. Off. . |
| 52-48488 U | 4/1977 | Japan . |

*Primary Examiner*—Thomas G. Wyse

[57] ABSTRACT

A filler-packing apparatus comprises a bundled filler-receiving space assembly, a movable bottom stopper assembly having bottom stoppers which are insertable into bottom openings of the filler-receiving spaces of said assembly, and top stoppers which are respectively insertable into top openings of the filler-receiving spaces and enabling packing filler in a plurality of columns in a short period of time. A filler-packing method uses this apparatus and thereby enables packing of the filler into the filler-receiving spaces in short period of time uniformly. An assembly of columns is uniformly packed with a filler and assembled by using the filler-packing apparatus and the filler-packing method.

9 Claims, 4 Drawing Sheets

FILLER-PACKING APPARATUS, FILLER-PACKING METHOD, AND FILLER-PACKED COLUMN ASSEMBLY

This application is the national phase under 35 U.S.C. §371 of prior PCT International Application No. PCT/JP96/03708 which has an International filing date of Dec. 19, 1996 which designated the United States of America, the entire contents of which are hereby incorporated by reference.

FIELD OF THE INVENTION

This invention relates to a filler-packing apparatus, a filler-packing method, and a filler-packed column assembly. More specifically, this invention relates to a compact space-saving filler-packed column assembly, which can suitably be used for a simulated moving bed separation apparatus for instance, a filler-packing apparatus, which enables efficient, rapid and uniform packing of a filler in each column of the filler-packed column assembly as well as a method of efficiently, rapidly, and uniformly packing the filler in each column of the filler-packed column assembly.

BACKGROUND OF THE INVENTION

The simulated moving bed separation apparatus comprises a circulation fluid passage, which is formed by endlessly connecting a plurality of beds packed with a separation filler. A circulation fluid circuit is provided with an eluent inlet for introducing an eluent, an extract outlet for discharging a solution rich in adsorbable substances or strongly adsorbable substances, a stock solution inlet for introducing a stock solution containing a mixture of components, which are to be separated, and a raffinate outlet for discharging a solution rich in non-adsorbable or weakly adsorbable substances sequentially in this order in the direction of the fluid flow, wherein the inlets and outlets are successively shifted intermittently.

In the simulated moving bed separation apparatus, there are provided a desorption zone (IV), which comprises filler beds placed between the eluent inlet and the extract outlet, wherein the separation filler retaining a concentrated adsorbed or strongly adsorbed components is contacted with an eluent and the adsorbed or strongly adsorbed components are expelled from the separation filler; a concentration zone (III), which comprises filler beds placed between the extract outlet and the stock solution inlet, wherein the non-adsorbable or weakly adsorbable components remaining on the separation filler are expelled and the adsorbable or strongly adsorbable components are concentrated; a refining zone (II), which comprises filler beds placed between the stock solution inlet and the raffinate outlet, wherein the stock solution is contacted with the separation filler and adsorbable or strongly adsorbable components are adsorbed on the separation filler and non adsorbable or weakly adsorbable components are recovered with the eluent; and an adsorption zone (I), which comprises filler beds placed between the raffinate outlet and the eluent inlet, wherein the non-adsorbable or weakly adsorbable components are adsorbed on the separation filler and the eluent, in which the non-adsorbed or weakly adsorbed components are depleted, is recovered.

When a simulated moving bed separation apparatus is assembled, a separation filler, which separates the components to be separated, must be packed into columns first of all.

Conventionally, columns are packed with a filler one by one and the packed columns are inspected one by one. More specifically, there are dry method and wet method for packing columns in filler packing.

In the case of the wet packing, a column, which is a cylinder, is positioned upright and an end stopper is fixed to the bottom opening at the bottom end thereof. The top end of the column is connected to the bottom opening of a reservoir tank. Thus the inside space of the column is communicated with the reservoir tank. When the column is connected to the reservoir tank, it is still empty. The reservoir tank is provided with a closable slurry-introducing inlet and a solvent-supplying inlet at the top thereof. A column is connected to the reservoir tank and the slurry-introducing inlet of the reservoir tank is opened to allow the slurry to flow into the reservoir tank.

In this connection, a slurry suitable for wet packing is the one comprising a filler having an average particle diameter of about 50 $\mu$m dispersed in a dispersion solvent at a concentration of 10–60 wt/vol %. Then the slurry-introducing inlet is closed and a dispersion solvent is forcibly introduced into the reservoir tank through the solvent-supplying inlet. The forced introduction of the dispersion solvent promotes settling of the filler in the slurry in the reservoir tank and the column. After the filler has fully settled, the forced introduction of the dispersion solvent is stopped and the column is removed from the reservoir tank. Thereafter, the top opening of the column is tightly closed with a removable stopper or a fixed stopper.

In the dry packing, a column, which is a cylinder, is positioned upright, an end stopper is fixed to an end stopper opening. Then powder of a filler having a large average diameter (at least far larger than the filler dispersed in the slurry to be used in wet method) is poured into the column. The filler is poured into the column up to the level of the top opening of the column and then the column is subjected to vibration. The vibration can be applied to the column from the beginning of pouring the filler powder. When the vibration is applied to the column, the filler packed up to the level of the top opening thereof is further compacted and sinks and a void space appears at the top of the column. The filler is further supplied into this space. At the time when the filler no longer sinks even if the filler is added under vibration, the vibration and pouring of the filler are stopped. The top opening of the column is closed with an end stopper.

The simulated moving bed separation apparatus is usually provided with 8, 12, 16 or 24 or more columns. It is time-consuming to manually pack such numbers of columns one by one. Suppose that it takes one hour to pack a column with a filler, it will take 16 hours to pack the columns and prepare a simulated moving bed separation apparatus provided with 16 columns to the condition for operation. This is very inefficient. The above-mentioned one hour for instance is the shortest time when a worker exclusively devotes himself to the packing work. In the practical operation, however, the packing work is accompanied by various incidental operations and, therefore, it takes far more time. That is, it is troublesome, complicated, and time-consuming to manually pack columns one by one. When 16 columns are packed for instance, it is difficult in fact to uniformly and evenly pack all the 16 columns. The packing density of the first column and that of the 16th columns are often different. It is considered that it is because the filler concentration in a slurry changes in a long operation time required for packing operation. Even if 16 columns are packed with a filler by the troublesome and complicated column-by-column operation, the apparatus cannot be used until each column is tested and evaluated for its performance.

In a conventional simulated moving bed separation apparatus, a circulating fluid passage is formed by connecting a plurality of columns end-to-end with conduits and all the columns are arranged in a line for instance. Therefore, the apparatus is inevitably of a large size requiring some space.

The object of this invention is to provide a filler-packing apparatus, a filler-packed column assembly, and a filler-packing method, which solve the above-described problem. In other words, the object of the invention is to provide a filler-packing apparatus, which enables uniformly packing filler into columns by simple operation within a short period of time, a filler-packing method using said apparatus and a compact assembly of columns uniformly packed with filler.

DISCLOSURE OF THE INVENTION

The first invention, which solves the foregoing problem, is a filler-packing apparatus that comprises:

(a) a filler-receiving space assembly having a plurality of upright cylinders which are filler-receiving spaces respectively having a top opening and a bottom opening; or a filler-receiving space assembly having a plurality of filler-receiving spaces respectively formed by longitudinally boring through a pillar block from a top opening at the top end surface thereof to a bottom opening at the bottom end surface thereof;

(b) a movable bottom stopper assembly having bottom stoppers which are liquid-tightly fixable to the bottom openings of the filler-receiving spaces and are respectively provided with a porous body; a base member, which is positioned under the filler-receiving space assembly and holds the bottom stoppers in the upright position at the positions respectively corresponding to the bottom opening of the respective filler-receiving spaces; and conduits which are respectively connected to the bottom stoppers so that they communicate with the bottom stoppers;

(c) top stoppers which are respectively a hollow cylinder liquid-tightly fixed to the top opening of the filler-receiving spaces and provided with a porous body inside thereof; and (d) a securing means for connecting the filler-receiving space assembly and the movable bottom stopper assembly under the condition that the bottom stoppers are inserted in the bottom openings of the filler-receiving spaces.

The second invention, which solves the above-described problem, is a filler-packing method that comprises:

using (a) the filler-receiving space assembly and (b) the movable bottom stopper assembly of the first invention, inserting a part of each of the bottom stoppers into each of the bottom openings of the filler-receiving spaces; pouring a filler-containing slurry into the filler-receiving spaces through the top openings of the filler-receiving spaces;

inserting the top stoppers in the top openings after the filler in the slurry has sunken in the filler-receiving spaces; and securing the movable bottom stopper assembly to the filler-receiving space assembly by means of a securing means.

The third invention, which solves the above-described problem, is a filler-packing method that comprises:

using (a) the filler-receiving space assembly, (b) movable bottom stopper assembly, and (c) the top stoppers of the first invention, inserting a part of each of the bottom stoppers into each of the bottom openings of the filler-receiving spaces; introducing a filler powder into the filler-receiving spaces through the top openings of the filler-receiving spaces; applying vibration to the filler-receiving space assembly, and thereafter inserting the top stoppers in the top openings and fixing them; and securing the movable bottom stopper assembly to the filler-receiving space assembly by means of a securing means.

The fourth invention, which solves the above-described problem, is a filler-packed column assembly that comprises:

(a) the filler-receiving space assembly, (b) the movable bottom stopper assembly, and (c) the top stoppers of said first invention;

wherein the bottom stoppers are respectively inserted in the bottom openings of the filler-receiving spaces and the bottom stoppers are liquid-tightly fixed to the bottom openings of the filler-receiving space assembly so that no fluid leaks out of the filler-receiving spaces; the filler-receiving spaces are packed with a filler, and the top stoppers are liquid-tightly fixed on the top openings of the filler-receiving spaces.

BEST MODE OF WORKING THE INVENTION

1. Filler-Packing Apparatus

Figure 1:
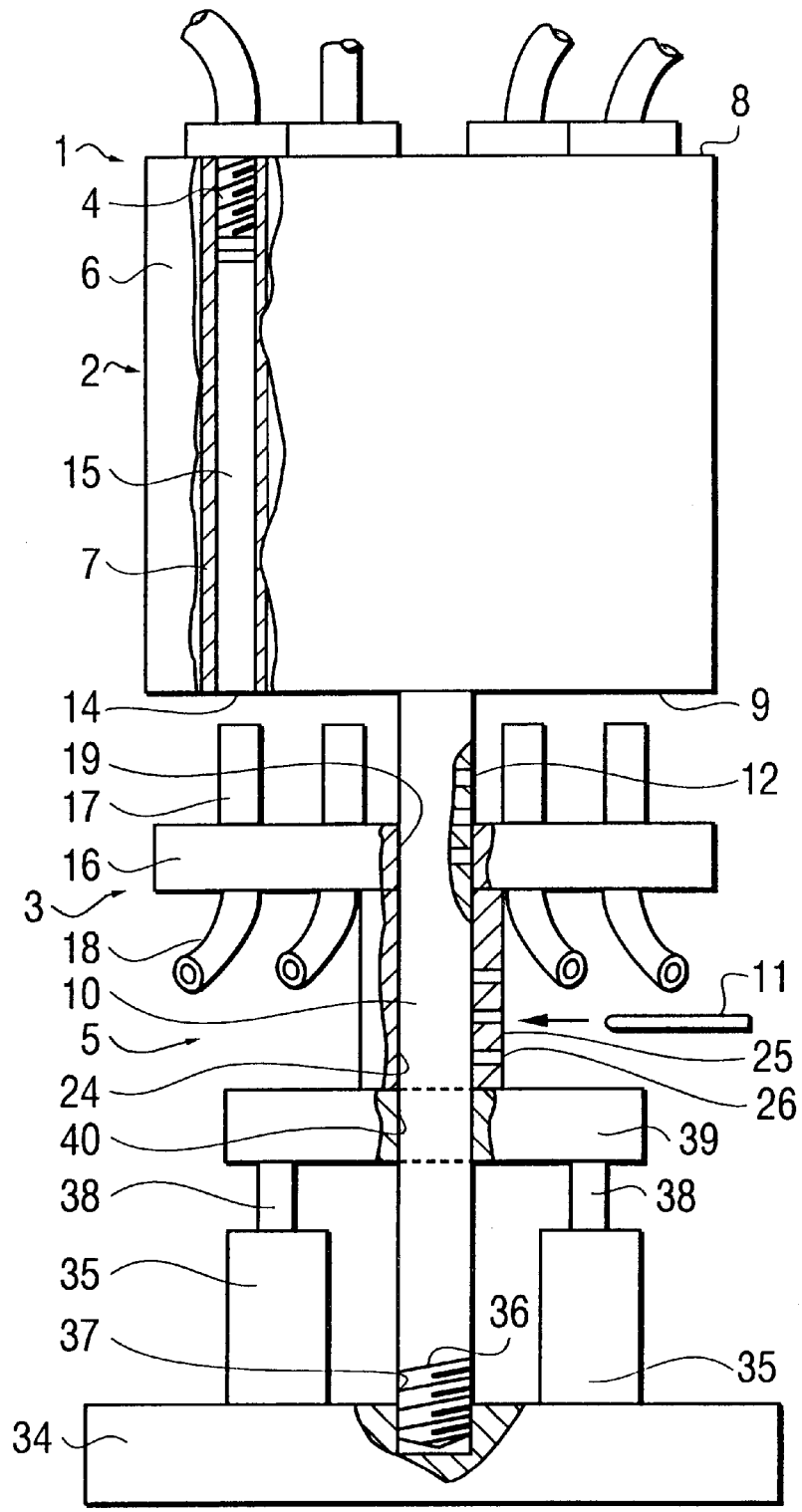
FIG. 1 is a partly cross-sectional front view of a filler-packing apparatus as an embodiment of the present invention.

The filler-packing apparatus fundamentally comprises a filler-receiving space assembly, a movable bottom stopper assembly and a securing means.

(a) Filler-Receiving Space Assembly

The filler-receiving space assembly has a required number of filler-receiving spaces wherein a separation filler can be packed. The filler-receiving space means a space where a filler is packed. The filler-receiving space is an inside space of tubular body having a predetermined axial length or a hollow space bored in a pillar block having a predetermined axial length. Therefore, a preferable example of the filler-receiving space assembly is an assembly comprising a plurality of bundled tubular bodies (called "tube bundle" in some cases) or an assembly of bores provided in a pillar block such as cylindrical or polygonal pillar block (usually a cylinder is preferred) extending from the top opening in the top surface to the bottom opening in the bottom surface (called "bore assembly" in some cases).

(a-1) Tube Bundle

The tube bundle comprises a plurality of bundled tubes. Each tube is a tubular body having an inside space for containing filler to work as a column. The tube bundle is usually used in the upright position with the axis in the vertical direction. Therefore, the bottom side opening is designated as a bottom opening and the top side opening is designated as a top opening.

In the tubular bodies, that is, in the filler-receiving spaces, a filler is packed as described later. When the tubular bodies are used for a simulated moving bed separation apparatus, various fluids flow under a predetermined pressure. Therefore, the tubular bodies are required to have a chemical resistance to withstand the corrosion by the flowing liquid, a sample solution containing components to be separated and a pressure resistance to withstand the fluid pressure.

Thus the tubular bodies are preferably made of a material having at least a chemical resistance and a pressure resistance. Such a material is suitably selected from metals, ceramics, synthetic resins, etc. Generally, preferred metallic materials for tubular bodies are steels such as stainless steels (JIS SUS series). Specifically, when a drug stock material flows, stainless steels (JIS—SUS series) are preferably used for tubular bodies. In cases such that the tubular bodies are made of a material having no chemical resistance, it is all right if the inside surface thereof is lined with a material having a chemical resistance, such as glass.

The dimensions of the tubular body such as inside and outside diameters, length, etc. are decided depending upon what fluid flows in the columns and what filler is packed. The dimensions are suitably determined in the designing of the apparatus.

The plurality of tubular bodies are preferably bundled so that the bottom openings thereof are arranged in a plane. If the tubular bodies are bundled with the bottom openings in a plane, connecting of the movable bottom stopper assembly and the filler receiving space assembly can be easily effected as described below and the bottom openings and the movable bottom stopper body can easily be connected without selective fitting when the bottom stoppers of the movable bottom stopper assembly are inserted into the bottom openings.

In some cases, however, the bottom stoppers of the filler-receiving space assembly are selectively connected to the plurality of tubular bodies of the filler-receiving space assembly. When a particular tubular body and a particular bottom stopper in the movable bottom stopper assembly are selectively combined, the plurality of tubular bodies need not be bundled so that the bottom openings are in a plane.

The plurality of tubular bodies are preferably bundled so that the top openings are in a plane. A preferred tube bundle is constructed with a plurality of tubular bodies having the same axial length bundled upright so that the bottom openings are in a plane.

In a tube bundle, the number of tubular bodies is not particularly restricted. The number can suitably be determined by considering for what purpose the filler-packed column assembly having the tube bundle is used. When the filler-receiving column assembly is used as columns for a simulated moving bed separation apparatus for instance, the number of tubular bodies in the tube bundle is a number as required for forming an adsorption zone, a concentration zone, a desorption zone, and a refining zone. The number of the columns required for these zones is usually 8, 12, 16, etc. It is not necessarily a multiple of 4.

At the top opening of the tubular bodies (which means the top opening when the tubular bodies stand upright, i.e. the opposite side openings of the bottom openings wherein the bottom stoppers of the movable bottom stopper assembly are inserted), the top stoppers are firmly mounted.

When a top stopper is mounted on one top opening, a connecting means, which firmly connects the top stopper and the top opening so that they cooperate, should preferably be provided. A combination of a female screw provided at the inside surface of the top opening and a male screw provided on the top stopper can be referred to as such a connective means. When the top stoppers are assembled to form a movable top stopper assembly and the top openings of the tubular bodies and the top stoppers are to be firmly connected by firmly connecting this movable top stopper assembly and the tube bundle, a connecting means, which enables the tube bundle and the movable top stopper assembly to firmly connect themselves in cooperation, should preferably be provided. A bolt-nut combination, a combination of a bolt and a screwed bolt hole, and other known connecting means, which connect the tube bundle and the movable top stopper assembly, can be referred to as such connecting means.

In the tube bundle, a heat medium conduit for keeping the tubular bodies at a predetermined temperature or a means for warming the tubular bodies can be provided. As such warming means, an insulating material surrounding the tubular bodies, a Dewar bottle-like double sleeve vacuum vessel having mirror inside surface, etc. can be referred to. Also to this tube bundle, incidental devices or equipment can be mounted, which are necessary for a simulated moving bed separation apparatus for instance, to which a filler-packed column assembly is incorporated.

(a-2) Bore Assembly

A bore assembly comprises a pillar block having a plurality of bores drilled therethrough from one end surface to the other in the axial direction.

The bores are made into columns by packing a filler. The filler is packed in the bores as described later. When a simulated moving bed separation apparatus using the bore assembly is operated, various fluids flow through the bores under a predetermined pressure. Therefore, the pillar block is required to have a chemical resistance to withstand the corrosion with the flowing fluids and a pressure resistance to withstand the fluid pressure.

Therefore, the pillar block is preferably made of a material having a chemical resistance and a pressure resistance. It will be suitably selected from metals, ceramics, synthetic resins, etc. Specifically, if drug stocks are passed therethrough, stainless steels, etc. will suitably be used for the pillar block. If the pillar block cannot be made of a material having a chemical resistance for some reason, however, the inside surface of the bores drilled through a pillar block will be preferably lined with a material having a chemical resistance such as glass.

The dimensions such as the inside and outside diameters, length, etc. of the bores will be suitably determined depending on what kind of fluid passes through the columns and what kind of filler is packed. Such dimensions are suitably set in the stage of the apparatus designing.

Both end surfaces of a pillar block should preferably be a flat plane. The reason why both end surfaces should preferably be a flat plane, is the same as that why the bottom openings of the tubular bodies in the tube bundle are in a flat plane.

The number of the drilled bores in the bore bundle is the same as the number of the tubular bodies in the tube bundles.

In the top openings of the bores (The term means the opening at the top of the pillar block when it stands upright with the axis thereof in the vertical direction. In other words, it means the end opening of the pillar block on the opposite side of the end opening of the movable bottom stopper assembly, where a porous body is to be inserted), top stoppers are firmly fixed. When the top stoppers are fixed to the respective top openings of the bores, a connecting means, which firmly connects the top opening of the bore and the top stopper in a mutual cooperative relation, should preferably be provided. As such connective means, a combination of a female screw thread provided in the inside surface of the top opening of the bores and a male screw thread provided on the top stopper can be referred to. When the top stoppers are bundled to form a movable top stopper assembly and the top stoppers are to be firmly connected to the top openings of the bores by firmly connecting the movable top stopper assembly and the bore bundle, preferably a connecting means, which firmly connects the bore bundle and the movable stopper assembly in a mutual cooperative relation, should preferably be provided. As such connecting means, a bolt-nut combination, which connects the bore bundle and the movable top stopper assembly, and other known connecting means can be referred to.

It is preferred to provide a heat exchange medium passage bores in the pillar block to regulate the temperature of the bores as predetermined. In some cases, a heat-insulating means can be provided on the outside or in the interior of the pillar block. Or a bore or bores, a hole or holes, through-hole or through-holes, or a groove or grooves for placing insulating materials can be provided in the pillar block. The insulating means are the same as those for the tube bundle or inferable therefrom.

(b) Movable Bottom Stopper Assembly

The above-described movable bottom stopper assembly has bottom stoppers placed at the positions corresponding to the bottom openings of the tubular bodies of the tube bundle; or bottom stoppers placed at the positions corresponding to the bottom openings of the bore bundle; a base member which supports the bottom stoppers upright; and conduits which respectively communicate with the bottom stoppers.

Specifically, a suitable movable bottom stopper assembly has a base member which has a flat top surface, bottom stoppers supported upright by the base member at the positions corresponding to the bottom openings of the tubular bodies of the tube bundle, and conduits which communicate with the bottom stoppers.

The bottom stoppers are fixed liquid-tight to the bottom openings of the tubular bodies or the bottom openings of the bores of the bore bundle and work to let the liquid in the slurry retained in the filler-receiving spaces to pass through into the conduits but to prevent the filler from coming out. Insofar as the bottom stopper has such a function, it can be of various structures. As a preferable structure, a structure comprising a cylindrical tubular body which can be fixed liquid-tight to the bottom opening of tubular body of the column, a porous body inserted in the inside of the cylindrical tubular body and a conduit connected to the end portion of the cylindrical tubular body can be referred to.

As materials for the porous body, various materials can be used insofar as they allow passing of liquid but prevent the filler from coming out and has a chemical resistance to the liquid to be separated with the filler-packed column assembly, and ceramics such as glass, a sintered body of metal powder, synthetic resins, i.e., polyolefins such as polyethylene, polypropylene, etc., polyamides such as nylon, fluorine resins such as Teflon, etc. can be referred to.

The bottom stopper may be of a structure having a porous body which is pillar-shaped body insertable in the bottom opening of the tubular body, a means fixing the porous body to the base member, and a conduit communicating with the porous body.

The bottom stopper is preferably provided with an O-ring made of a material, which can form liquid tight sealing, such as fluorine resins (Byton, for instance) so that the bottom stopper can be inserted liquid-tight in the bottom opening, whatever structure the bottom stopper may have.

The bottom stopper is preferably provided with a protective guide ring made of a soft synthetic resin such as Teflon on the inside wall of the end portion of the bottom opening so that the bottom stopper can be smoothly inserted in the bottom opening without scratching the inside wall of the bottom opening. If a protective guide is mounted on the end portion of the bottom stopper, the bottom stopper can be smoothly inserted into the bottom opening.

The conduit to be fixed to the bottom stopper has a function of allowing a liquid to pass through, more specifically, works as a drain passage for the liquid, which has been expelled from the slurry in the filler-receiving space when the filler is in the filler-receiving space, works as a part of the passage of the circulating fluid in a filler-packed column assembly in a simulated moving bed separation apparatus incorporating the former for instance.

The base member is a base on which said porous body and the conduit are fixed. Therefore, the base member may be a disc or a frame to which the bottom stoppers can be fixed.

(c) Top Stopper

The top stopper is inserted in the top opening of the filler-receiving spaces, has functions of at least expelling the liquid when the filler is packed after the top stopper has been inserted, firmly retain the packed filler when the filler-packed column assembly is used.

The top stopper has the structure suitably designed to have the above-described function, a structure comprising a cylindrical tubular body with a conduit fixed thereto at one end and a porous body inserted in the cylindrical tubular body for instance. The top stopper of this structure has a liquid-tight seal member to mount the top stopper on the top opening liquid-tightly. This seal member is suitably mounted at a suitable position to prevent leak of the liquid through the clearance of the top stopper inserted in the top opening. When an O-ring is used as a liquid-tight sealing member, the O-ring can be mounted on the outside of the cylindrical tubular body.

The top stopper is preferably fixed to the tubular body by means of a securing means so that the top stopper does not come off the filler-receiving space when the liquid in the slurry in the filler-receiving space is discharged by fixing the bottom stopper to the filler-receiving space assembly after the filler has been packed in the filler-receiving space. As fixing means, if the top stopper has a cylindrical tubular body as described above, a combination of a male screw thread formed on the outside of the cylindrical tubular body and a female screw thread formed in the inside surface of the top opening of the filler-receiving space can be referred to and other means can be suitably used.

The conduit fixed to the cylindrical tubular body has a function to allow a liquid to pass through, more particularly, works as a drain passage for the liquid, which has been expelled from the slurry in the filler-receiving space when the filler is in the filler-receiving space, and works as a part of the passage of the circulating fluid in a filler-packed column assembly in a simulated moving bed separation apparatus incorporating the former for instance.

The porous body inserted in the cylindrical tubular body has the same function as that of the porous body mounted on the bottom stopper. Therefore, the same materials as those for the porous body used for the bottom stopper can be used. When the porous body projects from the opening of the cylindrical tubular body or the cylindrical tubular body is not used, an annular protective guide ring made of a soft synthetic resin such as Teflon, etc. is mounted on the end of the porous body, and when the porous body is inserted in the cylindrical tubular body so that the end of said porous body and the end of the cylindrical tubular body are on the same plane, it is preferred to mount an annular protective ring made of a soft synthetic resin such as Teflon on the end of said cylindrical tubular body. By mounting the protective ring, the porous body or the cylindrical tubular body can be easily inserted into the bottom opening.

A plurality of top stoppers to be inserted in the top openings of the filler-receiving spaces can be prepared individually and independently. In such a case, the top stoppers are mounted respectively on a plurality of the top openings one by one.

In order to eliminate this inconvenience, a movable top stopper assembly, which comprises a base member, to which a plurality of top stoppers to be inserted in the top openings are fixed for instance, can be advantageously used.

More specifically, the movable top stopper assembly comprises a base member, on which a plurality of top stoppers are supported upright to the flat plane thereof at the positions which correspond to the top openings. In this case, although the porous bodies having a shape suitable for insertion into the top openings can be directly supported upright on the flat surface of the base member, usually cylindrical tubular bodies are supported on the flat surface of the base member and the porous bodies can be inserted into the cylindrical tubular body. In any case, preferably an annular protective guide tube made of a soft synthetic resin such as Teflon is mounted on the end (bottom end) of the porous body having a shape suitable to be inserted in the top opening or in the end (bottom end) of the cylindrical body having a shape suitable to be inserted into said top opening.

When the movable top stopper assembly is used, preferably a securing means which firmly connect the filler-receiving space assembly and the movable top stopper assembly should be employed in order to connect the filler-receiving space assembly and the movable top stopper assembly firmly and integrally when the filler is packed or when the filler-packed column assembly is used. The securing means can suitably be structured.

(d) Securing Means

This securing means firmly connects the movable bottom stopper assembly, whose bottom stoppers have been partly inserted into the bottom openings, and the filler-receiving space assembly and enables the bottom stoppers to completely penetrate into the bottom openings.

For the securing means, any structure can be employed if it has such a function. As such securing means, a mechanism which completely inserts the bottom stoppers into the bottom openings of the filler-receiving space assembly by moving the movable bottom stopper assembly toward the bottom openings of the filler-receiving space assembly which stands still; or a mechanism which enables the bottom stoppers to completely penetrate into the bottom openings by arranging the movable bottom stopper assembly in the state in which the bottom stoppers stand upright and fixing it, and lowering the filler-receiving space assembly, which is arranged such that the bottom openings face downward, toward the bottom stopper assembly, etc. can be referred to.

More specifically, a preferred example of this securing means comprises a positioning means, which fixes the filler-receiving space assembly at a predetermined position so that the filler-receiving space assembly stands upright, in other words, the bottom openings thereof open downward, and a lift means which lifts the movable bottom stopper assembly, which is located under the bottom openings of the filler-receiving space assembly so that the bottom stoppers stand upright at the position respectively corresponding to the bottom openings of the filler-receiving space assembly, toward thereto.

Whichever type of securing means is employed, a guide means is preferably employed so that the filler-receiving space assembly or the movable bottom stopper assembly, which must move, rises and lowers smoothly without play.

The effect of the filler packing apparatus of the invention is made clear by the following description of the filler-packing method.

(2) Filler-Packing Method

The filler packing method of the present invention is carried out by using the filler packing apparatus in accordance with the present invention.

In the filler packing method of this invention, the filler-receiving space assembly, the movable bottom stopper assembly, and the movable top stopper assembly are prepared.

Either of the filler-receiving space assembly and the movable bottom stopper assembly is fixed at a predetermined position. The following description relates to the case where the filler-receiving space assembly is fixed. The filler packing method of this invention includes a wet method and a dry method. The following is a wet method.

In fixing the filler-receiving space assembly, the filler-receiving space assembly is fixed by means of a suitable fixing means so that the bottom openings open downward. Then the movable bottom stopper assembly is positioned under the filler-receiving space assembly so that the bottom stoppers stand upright and that they respectively come exactly under the bottom openings. Thereafter, the tips of the bottom stoppers are inserted into the bottom openings by lifting the movable bottom stopper assembly and retained in that state.

Then a filler-containing slurry is poured into the filler-receiving space assembly through the top openings thereof. After the slurry has been poured into all the filler-receiving spaces from the top openings, the filler in the slurry settles to form a supernatant.

After the filler-receiving spaces are allowed to stand still for a predetermined period of time, the top stoppers are mounted on the top openings. As the supernatant exists in the top portion of the filler-receiving spaces, insertion of the top stoppers can be smoothly effected. The top stoppers are inserted until the end of the stoppers reach the settled filler of the slurry in the filler-receiving spaces. The inserted top stoppers are fixed in the filler-receiving spaces lest the stopper should come off the top openings because of the inside pressure of the filler-receiving spaces. This fixation can be effected by screw engagement of the male screw provided on the outside of the top stoppers and the female screw provided in the inside surface of the filler-receiving spaces. Of course, the top stoppers can be fixed or connected to the filler-receiving spaces by any means other than the screw engagement.

After the top stoppers have been mounted on all the top openings, the bottom stoppers are inserted into the bottom openings by lifting the movable bottom stopper assembly by means of the securing means. When this securing means comprises a positioning means, which fixes the filler-receiving space assembly to a predetermined position, and a lift means, which lifts the movable bottom stopper assembly, the insertion of the bottom stoppers into the bottom openings is effected by this lift means. On the other hand, when this securing means comprises a positioning means, which fixes the movable bottom stopper assembly at a predetermined position, and a lift means which lowers the filler-receiving space assembly, the forced insertion of the bottom stoppers into the bottom openings is effected by means of this lift means.

As the bottom stoppers are inserted into the filler-receiving spaces, the liquid present in the filler-receiving spaces passes through the porous bodies of the top stoppers and the porous bodies of the bottom stoppers and by way of the conduits. In other words, the slurry in the filler-receiving spaces is pressed as the rising bottom stoppers, which penetrate into the bottom openings, press the slurry and the liquid is expelled through the porous bodies and the conduits of the top stoppers and simultaneously through the porous bodies and conduits of the bottom stoppers. The filler in the slurry in the filler-receiving spaces is retained by the porous body of the top stopper and that of the bottom stoppers and is not expelled nor flows out. The conduits of the bottom stoppers may remain open as described above, but it is preferable to shut the conduits of the bottom stoppers to prevent the liquid flow when the bottom stoppers are inserted into the bottom openings. Drying of the filler in the filler-receiving spaces is prevented by keeping the conduits closed.

The movable bottom stopper assembly is firmly connected to the filler-receiving space assembly by means of the securing means, which is operated over a predetermined period of time. By this, the slurry in the filler-receiving spaces is pressed and the liquid thereof is expelled though the conduits. The excess liquid is removed and thus the filler-packed column assembly comprising a plurality of columns packed with wet filler is prepared.

In the case of dry packing, the end portions of the bottom stoppers are partly inserted into the bottom openings of the filler-receiving spaces as described above, a filler-receiving space assembly with the top openings of the filler-receiving spaces in the open condition is formed at first.

Then dry powder of the filler is poured into the filler-receiving spaces from the top openings with vibration applied to the filler-receiving space assembly. A vibrator may be mounted on the filler-receiving assembly. Vibration can be applied from the beginning of the pouring of the filler or after the filler has almost been poured into the filler-receiving spaces.

Now the filler packing is described with respect to wet packing method wherein the movable bottom stopper assembly is fixed and the filler-receiving space assembly is moved (the filler-receiving space assembly is moved toward the movable bottom stopper assembly).

A movable bottom stopper assembly is fixed so that the bottom stoppers stand upright. Then the filler-receiving space assembly is positioned so that the bottom openings open downward and come to the positions exactly above the bottom stoppers of the movable bottom stopper assembly.

Thereafter, the filler-receiving space assembly is lowered so that the end portions of the bottom stoppers are inserted into the bottom openings of the filler-receiving spaces and the thus formed state is maintained.

Thus dry powder of a filler is poured into the top openings of the filler-receiving spaces and, thereafter, top stoppers are inserted into the top openings. The operation therefor is the same as described above.

After the top stoppers are fixed to all the top openings, the bottom stoppers are further pushed into the bottom openings by lowering the filler-receiving space assembly by means of the securing means. If the securing means comprises a positioning means, which fixes the movable bottom stopper assembly at a predetermined position, and a lift means which lowers the filler-receiving space assembly, the lowering of the filler-receiving space assembly is effected by the motion of the lift means.

The operation which lowers the filler-receiving space assembly and secures the filler-receiving space assembly to the movable bottom stopper assembly is the same as the operation which lifts the movable bottom stopper assembly and secures the movable bottom stopper assembly to the filler-receiving spaces.

The operation in the case of dry packing in which the movable bottom stopper assembly is fixed and the filler-receiving space assembly is moved will be readily understood from the above description and therefore, it is not explained in detail.

(C) Filler-Packed Column Assembly

The filler-packed column assembly can be prepared by using the above described filler-packing apparatus and employing the said filler packing method.

This filler-packed column assembly comprises a plurality of filler-receiving spaces.

Into the bottom opening of each of the filler-receiving spaces, bottom stoppers of the movable bottom stopper assembly are respectively inserted and conduits are respectively connected to the ends of the bottom stoppers. Into each of the top openings of the filler-receiving spaces, top stoppers are respectively inserted and conduits are connected to the ends of the top stoppers. The filler is packed in the space in the filler-receiving spaces between the top stoppers and the bottom stoppers.

When the filler-packed column assembly is used as columns of a simulated moving bed separation apparatus, conduits are connected to each of the filler-receiving spaces of the filler-packed column assembly so that the filler-receiving spaces form one circulation passage.

EXAMPLE

The invention is now described with respect to a filler-packing apparatus which is a working example of the invention.

As shown in FIG. 1, the filler-packing apparatus 1 has a filler-receiving space assembly 2, a movable bottom stopper assembly 3, top stoppers 4, and a securing means 5.

The filler-receiving space assembly 2 has a cylindrical container 6, eight tubular bodies 7, and heat medium conduits not shown. This cylindrical container 6 has a flat top surface 8 and a flat bottom surface 9.

Figure 2:
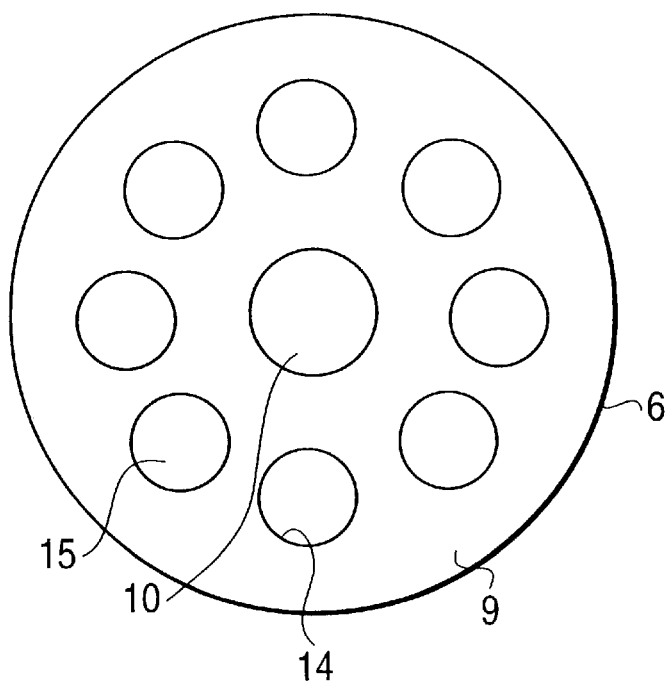
FIG. 2 is a bottom view of the filler-packing apparatus of FIG. 1.

As shown in FIGS. 1 and 2, a supporting rod 10 extends downward from the center of the bottom surface 9 of the container 6. This supporting rod 10 is provided with a male screw thread 36 at the lower end. On the surface of the supporting rod 10, a suitable number of small holes 12 for receiving positioning pins 11 are provided in a line.

Figure 3:
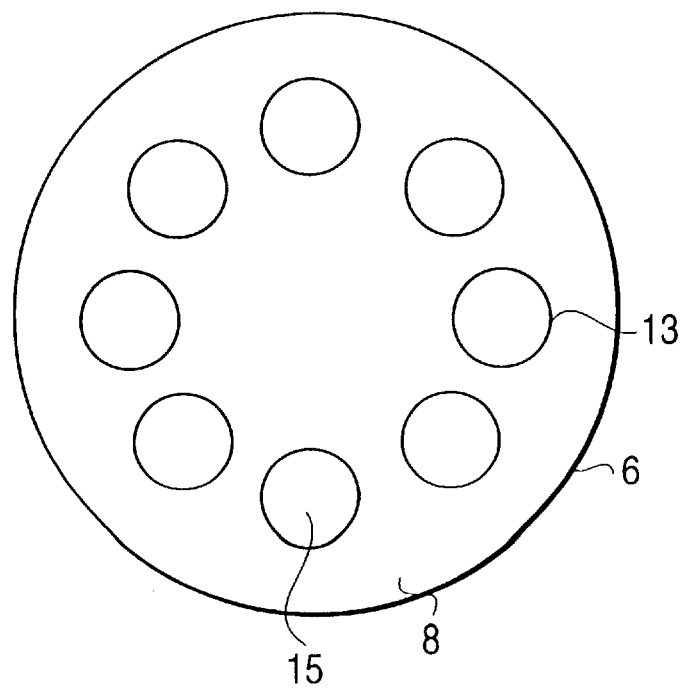
FIG. 3 is a top view of the filler-packing apparatus of FIG. 1.

On the top surface 8 of the container 6, as shown in FIG. 3, the top openings 13 of eight tubular bodies 7 open at the positions whereat the centers of the top openings 13 respectively correspond to the vertexes of a regular octagon. As shown in FIG. 2, also at the bottom surface 9 of the container 6, the bottom openings of the eight tubular bodies 7 open at the positions whereat the centers of the bottom openings 14 respectively correspond to vertexes of a regular octagon. Therefore, eight long tubular bodies 7 are arranged in the cylindrical container 6 so that they surround the central axes of the container 6 and the central axes of the tubular bodies 7 are parallel with the central axis of the cylindrical container 6. The inside spaces of the eight tubular bodies 7 constitute the filler-receiving space 15. The eight tubular bodies 7, respectively, have a female screw thread provided in the inside surfaces of the top openings 13.

The movable bottom stopper assembly 3 has a base member 16, bottom stoppers 17, and conduits 18.

The base member 16 is a disk whose top surface is flat and which is provided with a rod supporting hole 19 receiving and supporting the supporting rod 10. The base member 16 is further provided with eight through holes at the top side for supporting the bottom stoppers 17, which correspond to the bottom openings 14 of the tubular bodies 7 at the bottom surface 9 of the filler-receiving space assembly 2. In other words, at the top side of the base member 16, through-holes for receiving and supporting bottom stoppers are provided so that the centers of the through-holes for receiving and supporting the bottom stoppers form vertexes of a regular octagon and the distances between the centers of the through-holes for receiving and supporting the bottom stoppers and the center of the base member 16 are substantially equal to the distance between the center of the bottom opening of the tubular body 7 and the center of filler-receiving space assembly 2. At each of the through-holes for receiving and supporting the stoppers 17, the bottom stoppers 17 are mounted upright.

Figure 4:
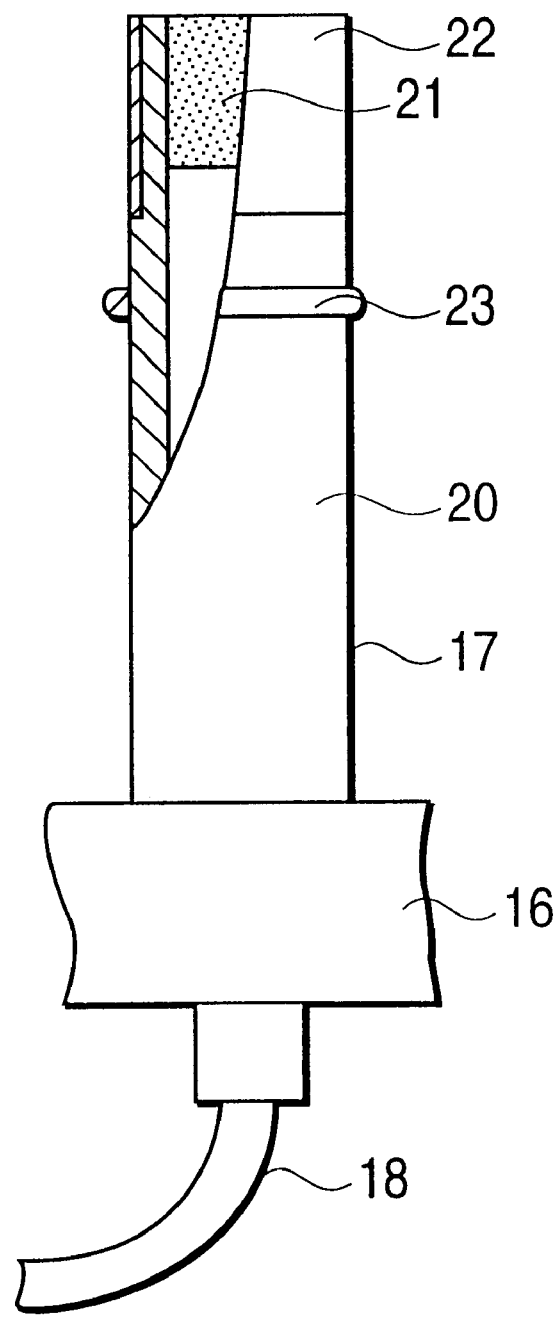
FIG. 4 is a partly cross-sectional front view of the bottom stopper provided in the filler-packing apparatus of FIG. 1.

The bottom stoppers 17 planted on the top side of the base member 16, as shown in FIG. 4, has a tubular sheath member 20 secured to the through-hole for receiving and supporting the bottom stoppers, a porous body 21 packed in the top opening of the sheath member 20, a protective guide tube of Teflon mounted on the outer surface of the top opening of the sheath member 20, and an O-ring 23 circumferentially mounted on the sheath member 20.

A conduit 18 is connected to the bottom end of the bottom stopper 17, which extends from the bottom side of the base member 16.

At the bottom side of the base member 16, a cylindrical body 25 provided with bores 24 having the same diameter as that of the rod-supporting hole 19 is secured. At the circumferential surface of the cylindrical body 25, through holes 26 for pins which penetrate the wall of the cylindrical body 25 are provided in a vertical file at the same intervals as those of the through-holes 12 for pins.

Figure 5:
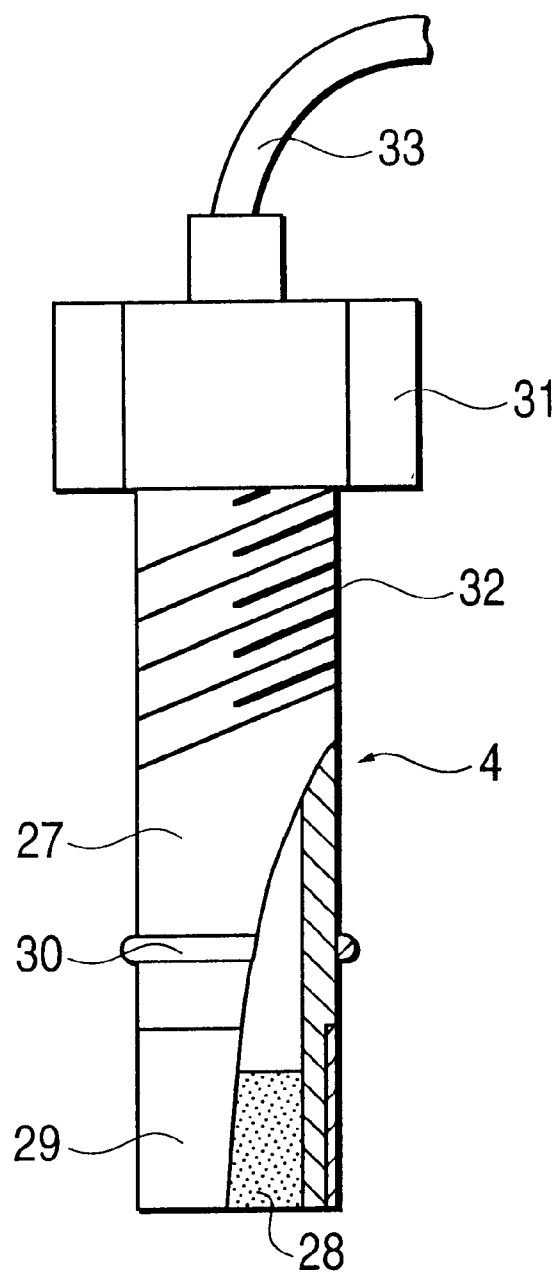
FIG. 5 is a partly cross-sectional front view of the top stopper of the apparatus of FIG. 1.

The top stopper 4, as shown in FIG. 5, has a cylindrical tubular body 27, a porous body 28 packed in the end opening of the cylindrical tubular body 27, a protective guide tube 29 of Teflon mounted on the outer surface of the top opening of the tubular body 27, an O-ring 30 circumferentially mounted at the central part of the cylindrical tubular body 27, a hexagonal bolt head 31 provided at the top of the cylindrical tubular body 27, and a conduit 33 connected to the bolt head 31. In the top stopper 4, a male screw thread 32 is provided on the circumferential surface from the base of the bolt head 31 to the central part of the cylindrical tubular body 27, and the male screw thread 32 engages with the female screw thread provided in the inside surface of the top opening 13 of the tubular body 7. The bolt head 31 is provided with a through-hole communicating the tubular body 7 and the conduit 33.

The securing means 5 in this example has a base 34 and jacks 35.

The base 34 is provided with wheels (not shown) and is able to move the securing means. In the top surface of the base 34, a receiving hole 37 having female screw thread, which engages with a male screw thread 36 provided on the lower surface of the supporting rod 10, in the inside thereof is provided. On the top surface of the base 34, a pair of jacks 35 are provided on both sides of the receiving hole 37. The jacks are operated by means of a hydraulic device and have a piston 38 which rises and falls. The two pistons 38 are spaced apart and the tops thereof support the operation disc 39. The operation disc 39 has a supporting hole 40 which receives the supporting rod 10. The operation disc 39 is provided at the position where the axis thereof in alignment with the centerline of the supporting hole 40. In other words, the operation disc 39 is supported by the pistons 38 so that the center line of the supporting hole 40 is in alignment with the centerline of the receiving hole 37.

An example of the method of this invention is carried out using the above-described filler-packing apparatus 1 as described below.

The base 34 of the securing means 5 is firmly fixed. The fixation of the base 34 can be effected by putting the brakes on the wheels of the base 34 or retracting the wheels into the bottom surface of the base and let the base 34 lie directly on the floor.

Then the movable bottom stopper assembly 3 is mounted on the operation disc 39 so that the central axis of the cylindrical body 25 is aligned with the central axis of the operation disc 39, and the bottom stoppers 17 stand upright. The supporting rod 10 is inserted in the cylindrical body 25 and the supporting hole 40, and the male screw 36 of the supporting rod 10 engages with the female screw of the receiving hole 37. Thus after the engagement, the cylindrical container 6 is mounted erect on the base 34 by means of the supporting rod 10.

In this state, the bottom stoppers 17 are properly positioned by horizontally rotating the movable bottom stopper assembly 3 around the supporting rod 10, for instance, so that the bottom stoppers 17, respectively, come to the positions of the bottom openings 14 of the tubular bodies 7.

When the bottom stoppers 17 are in the positions respectively just below the openings 14 of the tubular bodies 7, the jacks 35 are operated. When the pistons 38 are raised by the operation of the jacks 35, the top surface of the operation disc 39 contacts the bottom end of the cylindrical body 25 and the operating disc 39 lifts the cylindrical body 25. Thus the entire movable bottom stopper assembly 3 is lifted by the rising motion of the cylindrical body 25. The lifting of the movable bottom stopper assembly 3 makes the upper ends of the bottom stoppers 17 to get into the bottom openings 14 of the tubular bodies 7. When the bottom stoppers 17 are inserted in the tubular bodies 7 up to the position where the O-ring 23 is mounted, the movement of the jacks 35 is stopped.

At this stage, the bottom openings 14 of the tubular bodies 7 in the container 6 are closed with the bottom stoppers 17 and the top openings 13 remain open. The conduits 18 of the bottom stoppers 17 are put under the condition that passage of a fluid is prevented by means of a suitable closing means such as ball valve, pinch cock, etc. selected in accordance with the nature of the conduit material. In the inside space of the tubular body 7, a filler receiving space 15 is formed with the bottom formed by the bottom stopper 17.

Through the top openings 13 of the tubular bodies 7, which open at the top surface of the container 6, a slurry containing a filler is poured into all the tubular bodies 7. After pouring the slurry into all the tubular bodies 7, they are allowed to stand still to settle the filler and to form a supernatant in the top portion.

Thereafter, the top stoppers 4 are mounted at the top openings 13 of the tubular bodies 7. The ends of the top stoppers 4 are inserted into the top openings 13, and the female screw provided inside of the top openings 13 and the male screw 32 of the top stoppers 4 engage. By this screw engagement the operable top stoppers 4 are not pushed out even if the inside pressure of the filler receiving spaces 15 is excessively raised.

Then, the jacks 35 are operated to raise the pistons 38, and thus the motion of the piston 38 presses the bottom surface 9 of the cylindrical body 25 upward with the operating disc 39 and thus lifts the whole movable bottom stopper assembly 3. The lifting movement of the movable bottom stopper assembly 3 inserts the bottom stoppers 17 into the tubular bodies 7 through the bottom openings 14 thereof. Penetration of the bottom stoppers 17 into the filler-receiving spaces 15 compresses the filler present in the filler-receiving spaces 15 and the supernatant is expelled through the conduits 33 of the top stoppers 4, and the liquid present among the filler particles is also expelled through the conduits 33 of the top stoppers 4. At this step, if the conduits 18 communicating with the bottom stoppers 17 are made passable again by releasing the blocking means, the liquid is drawn out also through the conduits 18 of the bottom stoppers 17.

The jacks 35 are operated so that the operable bottom stoppers 17 are completely inserted into the bottom openings 14 and, thereafter, pins 11 are inserted into the through holes 26 provided in the cylindrical body 25 and the pin-receiving holes 12 provided in the supporting rod 10. By the insertion of the pins 11, the bottom stoppers 17 are fixed to the bottom openings 14 of the tubular bodies 7 and the movable bottom stopper assembly is tightly secured to the bottom surface of the container 6.

In this way, the top stoppers 4 are secured to the top openings 13 of the tubular bodies 7 in the container 6, the bottom stoppers 17 are secured to the bottom openings 14, the wet filler is packed in the filler-receiving spaces 15 defined by the top stoppers 4 and the bottom stoppers 17 in the tubular bodies 7, and thus, a filler-packed column assembly comprising integrated eight columns packed with wet filler are prepared.

The filler-packed column assembly is supported on the base by means of a supporting rod 10. However, the assembly can be removed from the supporting rod 10 and mounted on a simulated moving bed separation apparatus placed at another place, for instance.

In the above example,
(1) As eight tubular bodies are integrated in a container, packing of a filler into the tubular bodies can be effected by a suitable filler-packing operation even in a limited space.
(2) Instead of pouring a filler slurry into the tubular bodies, expelling the excess liquid and drying the wet filler in the tubular bodies one by one, the filler-containing slurry is poured into the eight tubular bodies one after the other, the entire excess liquid is pressed out simultaneously. Therefore, a filler-packed column assembly can be prepared in a very short period of time.
(3) As the filler is packed uniformly in the tubular bodies, there is no difference in packing densities between the first column and the 8th column as occurred in the conventional method.
(4) The removable bottom stoppers can be simultaneously inserted into the bottom openings of the tubular bodies by simply lifting the movable bottom stopper assembly. That is to say, the bottom stoppers can be fixed to the bottom openings of the tubular bodies without fail in a far shorter time than in case where the stoppers are fixed to the tubular bodies one by one.
(5) When the filler is packed into the tubular bodies using this filler-packing apparatus, the apparatus then works as a filler-packed column assembly. Therefore, the time required for preparing a simulated moving bed separation apparatus, for instance, to the working condition can be shortened.
(6) The filler-packed column assembly per se is compact and space-saving. Thus the simulated moving bed separation apparatus incorporating the filler-packed column assembly is compact. Therefore, the filler-packing apparatus has such and other various advantages.

Industrial Applicability

This invention provides a filler-packing apparatus which enables uniform packing of the filler in a plurality of columns in a short period of time by a simple operation; a filler-packing method which enables uniform packing of the filler by a simple operation in a short period of time using said apparatus and a small size filler-packed column assembly which is very compact and space-saving.

We claim:

1. A filler-packing apparatus, comprising:
   a filler-receiving space assembly having a plurality of upright filler-receiving spaces, each having a top opening and a bottom opening;
   a movable bottom stopper assembly having, bottom stoppers, each of said bottom stopper being provided with a porous body and liquid-tightly securable t o the bottom opening of each of said filler-receiving spaces; a base member positioned under said filler-receiving space assembly and holds said bottom stoppers at positions respectively corresponding to the bottoms of the respective filler-receiving spaces in the upright position; and conduits connected to said bottom stoppers so that said conduits communicate with said bottom stoppers;
   top stoppers provided with a porous body inside thereof, each top stopper being a hollow cylinder liquid-tightly fixed to the top opening of each of said filler-receiving spaces; and
   a unit adapted to insert said movable bottom stopper assembly in said filler-receiving space assembly and maintain said movable bottom stopper assembly in the inserted state.

2. A method for packing a filler by a filler-packing apparatus including a filler-receiving space assembly having a plurality of upright filler-receiving spaces, each having a top opening and a bottom opening; a movable bottom stopper assembly having bottom stoppers, each of said bottom stopper being provided with a porous body and liquid-tightly securable to the bottom opening of each of said filler-receiving spaces; and top stoppers provided with a porous body inside thereof, comprising:
   inserting each of said bottom stoppers into each bottom opening;
   pouring a filler-containing slurry into said filler-receiving spaces through the top opening of each of said filler-receiving spaces;
   inserting the top stoppers at each of the top openings after the filler in the slurry has sunken; and
   securing said movable bottom stopper assembly to said filler-receiving space assembly.

3. A filler-packing method that uses a filler-packing apparatus including a filler-receiving space assembly having a plurality of upright filler-receiving spaces, each having a top opening and a bottom opening; a movable bottom stopper assembly having bottom stoppers, each of said bottom stopper being provided with a porous body and liquid-tightly securable to the bottom opening of each of said filler-receiving spaces; and top stoppers provided with a porous body inside thereof, comprising:
   inserting each of said bottom stoppers into the bottom openings of said filler-receiving spaces;
   introducing a filler powder into said filler-receiving spaces through the top opening of each of said filler-receiving spaces;

applying vibration to the filler-receiving space assembly, and thereafter inserting the top stoppers at the top openings; and securing said bottom stoppers to said filler-receiving space assembly.

4. A filler-packed column assembly, according to claim 1, wherein said bottom stoppers are respectively inserted in the bottom openings of the filler-receiving spaces and the bottom stoppers are liquid-tightly fixed to the bottom openings, the filler-receiving spaces are packed with a filler, and the top stoppers are liquid-tightly inserted on the top openings of the filler-receiving spaces.

5. A filler-packing apparatus of claim 1, wherein said filler-receiving space is cylindrical in shape.

6. A filler-packing apparatus of claim 1, wherein said filler receiving space assembly has a plurality of filler-receiving spaces formed by longitudinally boring through a pillar block from the top to the bottom of the block.

7. A filler-packing apparatus of claim 1, wherein each of said bottom stoppers includes an O-ring adapted to liquid-tightly secure said bottom stopper to the bottom opening of each of said filler-receiving spaces.

8. A filler-packing apparatus of claim 1, wherein each of said top stoppers includes an O-ring adapted to liquid-tightly secure said top stopper to the top opening of each of said filler-receiving spaces.

9. A filler-packing apparatus of claim 1, wherein said unit includes a jack adapted to raise said movable bottom stopper towards said bottom opening.

* * * * *